US012653122B2

(12) United States Patent
Padilla

(10) Patent No.: US 12,653,122 B2
(45) Date of Patent: Jun. 16, 2026

(54) TRITICALE CULTIVAR APT1415420

(71) Applicant: Legacy Seeds Acquisitions Company 1, LLC, Butte, MT (US)

(72) Inventor: Racey Padilla, Vernon, TX (US)

(73) Assignee: Legacy Seeds Acquisition Company 1, LLC, Butte, MT (US)

( * ) Notice: Subject to any disclaimer, the term of this patent is extended or adjusted under 35 U.S.C. 154(b) by 327 days.

(21) Appl. No.: 17/932,144

(22) Filed: Sep. 14, 2022

(65) Prior Publication Data

US 2024/0081216 A1 Mar. 14, 2024

(51) Int. Cl.
*A01H 6/46* (2018.01)
*A01H 5/10* (2018.01)

(52) U.S. Cl.
CPC .............. *A01H 6/4678* (2018.05); *A01H 5/10* (2013.01); *A01H 6/463* (2018.05)

(58) Field of Classification Search
CPC ................................ A01H 6/4678; A01H 5/10
See application file for complete search history.

(56) References Cited

U.S. PATENT DOCUMENTS

| | | | |
|---|---|---|---|
| 5,969,219 A | 10/1999 | Nalepa et al. | |
| 7,307,202 B2 | 12/2007 | Matchett | |

OTHER PUBLICATIONS

Stitzer et al (Maize domestication and gene Interaction. New Phytologist, 220: 395-408, 2018) (Year: 2018).*
Oettler et al (Heterosis for yield and other agronomic traits of winter triticale F1 and F2 hybrids. Plant Breeding 120, 351-353, 2001) (Year: 2001).*
Meric et al (Profile-based proteomic investigation of unintended effects on transgenic and gamma radiation induced mutant soybean plants. Genet Resour Crop Evol 70: p. 2077-2095, 2023) (Year: 2023).*
Abuhammad et al., Plant variety protection certificate for Triticale 'APB249,' U.S. Department of Agriculture, Protection granted Jun. 4, 2021, PVPO No. 202000153, 12 pages.
Abuhammed et al., Plant variety protection certificate for Triticale 'APB269,' U.S. Department of Agriculture, Protection granted Jun. 4, 2021, PVPO No. 202000297, 12 pages.

Bruns, R., Plant variety protection certificate for Triticale 'SY 155T,' U.S. Department of Agriculture, Protection granted Jun. 25, 2014, PVPO No. 201200082, 15 pages.
Bruns, R., Plant variety protection certificate for Triticale 'SY 158T,' U.S. Department of Agriculture, Protection granted Jun. 25, 2014, PVPO No. 201200083, 15 pages.
Clark et al., Plant variety protection certificate for Triticale '641512175,' U.S. Department of Agriculture, Protection granted Apr. 26, 2021, PVPO No. 201700387, 10 pages.
Clark et al., Plant variety protection certificate for Triticale '841446398,' U.S. Department of Agriculture, Protection granted Apr. 26, 2021, PVPO No. 201700389, 10 pages.
Cunnigham, G., Plant variety protection certificate for Wheat, Common 'Camelot,' U.S. Department of Agriculture, Protection granted Aug. 7, 2009, PVPO No. 200900314, 30 pages.
Fohner, G., Plant variety protection certificate for Triticale '105,' U.S. Department of Agriculture, Protection granted Jun. 10, 2002, PVPO No. 9900400, 12 pages.
Fohner, G., Plant variety protection certificate for Triticale '348,' U.S. Department of Agriculture, Protection granted Jan. 13, 2003, PVPO No. 200200215, 9 pages.
Fohner, G., Plant variety protection certificate for Triticale '96,' U.S. Department of Agriculture, Protection granted Jun. 5, 2006, PVPO No. 200400002, 10 pages.
Houg, L., Plant variety protection certificate for Triticale 'SY TF 813,' U.S. Department of Agriculture, Protection granted Mar. 30, 2015, PVPO No. 201400329, 14 pages.
Rogers, T., Plant variety protection certificate for Triticale '946802617,' U.S. Department of Agriculture, Protection granted Mar. 21, 2018, PVPO No. 201600410, 9 pages.

* cited by examiner

*Primary Examiner* — Wayne Zhong
(74) *Attorney, Agent, or Firm* — McKee, Voorhees & Sease, PLC

(57) ABSTRACT

A *Triticale* variety, designated APT1415420, is disclosed. The invention relates to the seeds of *Triticale* cultivar APT1415420, to the plants of *Triticale* APT1415420, and to methods for producing a *Triticale* plant produced by crossing the cultivar APT1415420 with itself or another *Triticale* variety. The invention also relates to methods for producing a *Triticale* plant containing in its genetic material one or more transgenes and to the transgenic *Triticale* plants and plant parts produced by those methods. The invention also relates to *Triticale* varieties or breeding varieties and plant parts derived from *Triticale* cultivar APT1415420, to methods for producing other *Triticale* varieties, lines or plant parts derived from *Triticale* cultivar APT1415420, and to the *Triticale* plants, varieties, and their parts derived from the use of those methods. The invention further relates to hybrid *Triticale* seeds and plants produced by crossing the cultivar APT1415420 with another *Triticale* cultivar.

34 Claims, No Drawings

TRITICALE CULTIVAR APT1415420

TECHNICAL FIELD

The present disclosure relates to the field of plant breeding. In particular, this disclosure relates to a new and distinctive *Triticale* variety designated APT1415420

BACKGROUND

*Triticale* (*Triticale hexaploide* L.) is a crop species resulting from a cross between wheat (*Triticum*) and rye (*Secale*). It is a man-made crop in that plant breeders must physically make crosses and then manipulate the resultant offspring to obtain a self-fertile plant. Triticales are agronomically desirable due to their ideal combinations of the yield and quality advantages of common wheat, and the hardiness, pest tolerance, and adaptability of rye.

Hybrids of wheat and rye date back to the late 1800's, however early attempts to cross wheat and rye produced only sterile offspring, so for many years *Triticale* was only a scientific novelty. Fertile Triticales capable of producing viable seed were virtually unknown until the late 1930's when a Swedish geneticist named Arne Muntzing produced fertile *Triticale* by treating the hybrids with colchicines, which doubled the chromosome number allowing reproductive pairing and division to occur. With normal pairing and division, *Triticale* could be reproduced through subsequent generations. Once a fertile hybrid of *Triticale* was produced, it became possible to create new combinations between wheat and rye and to intercross *Triticale* with various common wheat. *Triticale* became a new crop plant, similar to, but distinct from common wheat, rye, and other cereal grains in breeding, seed production, and use. Once created and reproduced, a *Triticale* does not revert or break-down to its original wheat and rye components.

Most of the *Triticale* grown in the United States is used for feed grain and forage for swine, dairy cattle, and poultry. *Triticale* competes with other cereal grains, primarily common wheat and oats, for these forage markets. These markets in the U.S. are substantial. Cereal silage and hay are important in the major dairy producing regions, and cereal hay is a popular forage for horses.

*Triticale* is a cross between wheat as the female plant and rye as the pollinator. Compared to common wheat and oats, *Triticale* has important advantages for forage production in terms of yield, production costs, and tolerance to pests, drought, low fertility, mineral toxicities, and heavy grazing. *Triticale* is generally superior to all classes of common wheat for pasture, silage, hay, and for grain used for feed. Triticales, like common wheat, have either a winter or spring growth habit, but vary significantly in plant height, tend to tiller less, and have a larger inflorescence when compared with common wheat. The majority of *Triticale* cultivars have prominent awns, which sometimes cause problems in pastures or in hay. Certain releases are awnless and have increased its potential use as forage.

Common wheat and *Triticale* have many similarities in their pattern of plant development and morphology. The flower heads or spikes, develop at the top of the main stems and secondary stems called tillers, which are analogous to branches. An individual plant usually has a main stem and multiple tillers, the number of which depends on plant density, soil moisture, nutrient supply, pest damage, seeding date, and temperature, as well as the genetics of the plant. Typically, two to four tillers per plant will develop to the point of developing a head. Each head at the top of the stem consists of multiple spikelets, each of which consists of multiple florets that produce pollen, ovules, and ultimately, kernels.

*Triticale* has many benefits to offer crop producers, livestock feeders, and for commercial use in soft-dough mixtures. Its major strength is its versatility: it can be used for grazing, silage, feed, cover crops, straw, and even human consumption. Additionally, production of *Triticale* provides environmental benefits such as erosion control and improved nutrient cycling through crop rotation. Thus, because of its considerable benefits, significant plant breeding effort has been directed towards breeding *Triticale*.

Development of hybrid plant breeding has made possible considerable advances in quality and quantity of crops produced. Increased yield and combination of desirable characteristics, such as resistance to disease and insects, heat and drought tolerance, along with variations in plant composition are all possible because of hybridization procedures. These procedures frequently rely heavily on providing for a male parent contributing pollen to a female parent to produce the resulting hybrid.

Field crops are bred through techniques that take advantage of the plant's method of pollination. A plant is self-pollinated if pollen from one flower is transferred to the same or another flower of the same plant or a genetically identical plant. A plant is cross-pollinated if the pollen comes from a flower on a genetically different plant. In certain species, such as *Brassica campestris*, the plant is normally self-sterile and can only be cross-pollinated. In predominantly self-pollinating species, such as soybeans, wheat, and cotton, the male and female plants are anatomically juxtaposed such that during natural pollination, the male reproductive organs of a given flower pollinate the female reproductive organs of the same flower. *Triticale*, as with wheat, is predominantly self-pollinating, though considerable outcrossing may occur.

SUMMARY

Provided here is *Triticale* seed, a *Triticale* plant, plant parts, a *Triticale* cultivar and a method for producing a *Triticale* plant. Further provided are methods of producing *Triticale* seeds and plants by crossing a plant of the instant invention with another *Triticale* plant.

The compositions and methods relate to seeds of the novel *Triticale* line APT1415420, to the plants of *Triticale* line APT1415420 and to methods for producing a *Triticale* plant produced by crossing the *Triticale* APT1415420 with itself or another *Triticale* plant. Thus, any such methods using the *Triticale* line APT1415420 are part of this invention, including selfing, backcrosses, hybrid production, crosses to populations, and the like. This disclosure further relates to *Triticale* cultivar seeds, plants, and plant parts produced by crossing the *Triticale* cultivar APT1415420 or a backcross conversion of APT1415420 with another *Triticale* cultivar. Also provided are *Triticale* plants having the physiological and morphological characteristics of *Triticale* cultivar APT1415420.

In another aspect, single trait converted plants of APT1415420 are provided. The single transferred trait may preferably be a dominant or recessive allele. Preferably, the single transferred trait will confer such traits as herbicide resistance, insect resistance, resistance for bacterial, fungal, or viral disease, male fertility, male sterility, and industrial usage. The single trait may be a naturally occurring *Triticale* gene or a transgene introduced through genetic engineering techniques.

In another aspect is provided regenerable cells for use in tissue culture of *Triticale* plant APT1415420. The tissue culture will preferably be capable of regenerating plants having the physiological and morphological characteristics of the foregoing *Triticale* plant, and of regenerating plants having substantially the same genotype as the foregoing *Triticale* plant. Preferably, the regenerable cells in such tissue cultures will be embryos, protoplasts, meristematic cells, callus, plant clumps, pollen, ovules, pericarp, seeds, flowers, florets, heads, spikes, leaves, roots, root tips, anthers, stems, and the like. Still further, the present invention provides *Triticale* plants regenerated from the tissue cultures of the invention.

This disclosure further relates to methods for genetically modifying a *Triticale* plant of the variety APT1415420 and to the modified *Triticale* plants produced by those methods. The genetic modification methods may include, but are not limited to mutation, genome editing, RNA interference, gene silencing, backcross conversion, genetic transformation, single and multiple gene conversion, and/or direct gene transfer. The disclosure further relates to to genetically modified *Triticale* plant produced by the above methods, wherein the genetically modified *Triticale* plant comprises the genetic modification and otherwise all of the physiological and morphological characteristics of *Triticale* cultivar APT1415420.

The disclosure also provides methods of multiplication or propagation of *Triticale* plants of the disclosure, which can be accomplished using any method known in the art, for example, via vegetative propagation and/or seed. The disclosure also encompasses the plantlets and plants produced by those methods.

In a further aspect, the disclosure provides a method of producing a commodity plant product comprising collecting the commodity plant product from the plant of *Triticale* cultivar APT1415420. In some embodiments, the commodity plant product can be, but is not limited to, grain, flour, cereal, malt, silage, feed, or straw.

In addition to the exemplary aspects and embodiments described above, further aspects and embodiments will become apparent by study of the following descriptions.

DESCRIPTION

Provided here is *Triticale* seed, a *Triticale* plant, a *Triticale* line and a *Triticale* hybrid. This invention further relates to a method for producing *Triticale* seed and plants. All references cited in this application are herein incorporated by reference.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single cultivar an improved combination of desirable traits from the parental germplasm. In *Triticale*, the important traits include by way of example, increased yield and quality, resistance to diseases and insects, resistance to drought and heat, and improved agronomic traits.

When producing a line or variety, choice of breeding or selection methods depends on the mode of plant reproduction, the heritability of the trait(s) being improved, and the type of cultivar used commercially (e.g., $F_1$ hybrid cultivar, pureline cultivar, etc.). Popular selection methods commonly include pedigree selection, modified pedigree selection, mass selection, and recurrent selection.

The goal of a commercial *Triticale* breeding program is to develop new, unique and superior *Triticale* cultivars. The breeder initially selects and crosses two or more parental lines, followed by generation advancement and selection, thus producing many new genetic combinations. The breeder can theoretically generate billions of different genetic combinations via this procedure. The breeder has no direct control over which genetic combinations will arise in the limited population size which is grown. Therefore, two breeders will never develop the same line having the same traits.

Each year, the plant breeder selects the germplasm to advance to the next generation. This germplasm is grown under unique and different geographical, climatic and soil conditions, and further selections are then made, during and at the end of the growing season. The lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce, with any reasonable likelihood, the same cultivar twice by using the exact same original parents and the same selection techniques. This unpredictability results in the expenditure of large amounts of research moneys to develop superior new *Triticale* cultivars.

Pureline cultivars of *Triticale* are commonly bred by hybridization of two or more parents followed by selection. The complexity of inheritance, the breeding objectives and the available resources influence the breeding method. Pedigree breeding, recurrent selection breeding and backcross breeding are breeding methods commonly used in self-pollinated crops such as *Triticale*. These methods refer to the manner in which breeding pools or populations are made in order to combine desirable traits from two or more cultivars or various broad-based sources. The procedures commonly used for selection of desirable individuals or populations of individuals are called mass selection, plant-to-row selection and single seed descent or modified single seed descent. One, or a combination of these selection methods, can be used in the development of a cultivar from a breeding population.

Pedigree breeding is primarily used to combine favorable genes into a totally new cultivar that is different in many traits than either parent used in the original cross. It is commonly used for the improvement of self-pollinating crops. Two parents which possess favorable, complementary traits are crossed to produce an $F_1$ (filial generation 1). An $F_2$ population is produced by selfing $F_1$ plants. Selection of desirable individual plants may begin as early as the $F_2$ generation wherein maximum gene segregation occurs. Individual plant selection can occur for one or more generations. Successively, seed from each selected plant can be planted in individual, identified rows or hills, known as progeny rows or progeny hills, to evaluate the line and to increase the seed quantity, or, to further select individual plants. Once a progeny row or progeny hill is selected as having desirable traits it becomes what is known as a breeding line that is specifically identifiable from other breeding lines that were derived from the same original population. At an advanced generation (i.e., $F_5$ or higher) seed of individual lines are evaluated in replicated testing. At an advanced stage the best lines or a mixture of phenotypically similar lines from the same original cross are tested for potential release as new cultivars.

One method of breeding utilizes the single seed descent procedure which the strict sense refers to planting a segregating population, harvesting one seed from every plant, and combining these seeds into a bulk which is planted the next generation. When the population has been advanced to the desired level of inbreeding, the plants from which lines are derived will each trace to different $F_2$ individuals. Primary advantages of the seed descent procedures are to delay selection until a high level of homozygosity (e.g., lack of gene segregation) is achieved in individual plants, and to move through these early generations quickly, usually through using off-season nurseries.

Selection for desirable traits can occur at any segregating generation ($F_2$ and above). Selection pressure is exerted on a population by growing the population in an environment where the desired trait is maximally expressed and the individuals or lines possessing the trait can be identified. For instance, selection can occur for disease resistance when the plants or lines are grown in natural or artificially-induced disease environments, and the breeder selects only those individuals having little or no disease and are thus assumed to be resistant.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs). Such techniques are described further supra.

Molecular markers, which include markers identified through the use of techniques such as Starch Gel Electrophoresis, Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. For example, molecular markers are used in soybean breeding for selection of the traiAAt of resistance to soybean cyst nematode, see U.S. Pat. No. 6,162,967. The markers can also be used to select toward the genome of the recurrent parent and against the markers of the donor parent. Using this procedure can attempt to minimize the amount of genome from the donor parent that remains in the selected plants. It can also be used to reduce the number of crosses back to the recurrent parent needed in a backcrossing program. The use of molecular markers in the selection process is often called Genetic Marker Enhanced Selection. Molecular markers may also be used to identify and exclude certain sources of germplasm as parental varieties or ancestors of a plant by providing a means of tracking genetic profiles through crosses as discussed more fully hereinafter.

Mutation breeding is another method of introducing new traits into *Triticale* varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogues like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in "Principles of Cultivar Development" by Fehr, Macmillan Publishing Company, 1993.

The production of double haploids can also be used for the development of homozygous varieties in a breeding program. Double haploids are produced by the doubling of a set of chromosomes from a heterozygous plant to produce a completely homozygous individual. For example, see Wan et al., Theor. Appl. Genet., 77:889-892, 1989.

Descriptions of other breeding methods that are commonly used for different traits and crops can be found in one of several reference books (e.g., Allard, 1960; Simmonds, 1979; Sneep, et al. 1979; Fehr, 1987).

*Triticale* is an important and valuable field crop. Thus, a continuing goal of *Triticale* plant breeders is to develop stable, high yielding *Triticale* cultivars that are agronomically sound. The reasons for this goal are to maximize yield and the quality of the final product for forage, silage, and human consumption. To accomplish this goal, the *Triticale* breeder must select and develop plants that have the traits that result in superior cultivars. The development of new *Triticale* cultivars requires the evaluation and selection of parents and the crossing of these parents. The lack of predictable success of a given cross requires that a breeder, in any given year, make several crosses with the same or different breeding objectives.

The crossed or hybrid seed is produced by manual crosses between selected parents. Floral buds of the parent that is to be the female are emasculated prior to the opening of the flower by manual removal of the male anthers. At flowering, the pollen from flowers of the parent plants designated as male, are manually placed on the stigma of the previous emasculated flower. Seed developed from the cross is known as first generation ($F_1$) hybrid seed. Planting of this seed produces $F_1$ hybrid plants of which half their genetic component is from the female parent and half from the male parent. Segregation of genes begins at meiosis thus producing second generation ($F_2$) seed. Assuming multiple genetic differences between the original parents, each $F_2$ seed has a unique combination of genes.

The foregoing examples of the related art and limitations related therewith are intended to be illustrative and not exclusive. Other limitations of the related art will become apparent to those of skill in the art upon a reading of the specification. References cited herein are incorporated herein by reference.

In the description and tables which follow, a number of terms are used. In order to provide a clear and consistent understanding of the specification and claims, including the scope to be given such terms, the following definitions are provided:

Allele. Allele is any of one or more alternative forms of a gene, all of which alleles relate to one trait or characteristic. In a diploid cell or organism, the two alleles of a given gene occupy corresponding loci on a pair of homologous chromosomes.

Awn. Awn is intended to mean the elongated needle-like appendages on the flower and seed-bearing "head" at the top of the cereal grain plant (e.g., *Triticale*, common wheat, rye). These awns are attached to the lemmas. Lemmas enclose the stamen and the stigma as part of the florets. These florets are grouped in spikelets, which in turn together comprise the head.

Backcrossing. Backcrossing is a process in which a breeder repeatedly crosses hybrid progeny back to one of the parents, for example, a first generation hybrid $F_1$ with one of the parental genotypes of the $F_1$ hybrid.

Disease Resistance. As used herein, the term "disease resistance" is defined as the ability of plants to restrict the activities of a specified pest or pathogen, such as an insect, fungus, virus, or bacterial.

Disease Tolerance. As used herein, the term "disease tolerance" is defined as the ability of plants to endure a specified pest or pathogen (such as an insect, fungus, virus or bacteria) or an adverse environmental condition and still perform and produce in spite of this disorder.

Essentially all of the physiological and morphological characteristics. A plant having essentially all of the physiological and morphological characteristics means a plant having the physiological and morphological characteristics of the recurrent parent, except for the characteristics derived from the converted trait.

Stripe Rust. A disease of *Triticale*, common wheat, durum wheat, and barley characterized by elongated rows of yellow spores on the affected parts, caused by a rust fungus, *Puccinia striiformis*.

Head. As used herein, the term "head" refers to a group of spikelets at the top of one plant stem. The term "spike" also refers to the head of a plant located at the top of one plant stem.

Maturity. As used herein, the term "maturity" refers to the stage of plant growth at which the development of the kernels is complete.

Plant Height (Hgt). As used herein, the term "plant height" is defined as the average height in inches or centimeters of a group of plants.

As used herein, the term plant includes reference to an immature or mature whole plant, including a plant from which seed, grain, or anthers have been removed. A seed or embryo that will produce the plant is also considered to be a plant. Reference to a plant is used broadly herein to include any plant at any stage of development.

A plant part refers to any part of a plant, including a plant cutting, a plant cell, a plant cell culture, a plant organ, a plant seed, and a plantlet. Examples include, without limitation, protoplasts, callus, leaves, stems, roots, root tips, anthers, pistils, seed, grain, pericarp, embryo, pollen, ovules, cotyledon, hypocotyl, spike, floret, awn, lemma, shoot, tissue, petiole, cells, and meristematic cells. A plant cell is the structural and physiological unit of the plant, comprising a protoplast and a cell wall. A plant cell can be in the form of an isolated single cell or aggregate of cells such as a friable callus, or a cultured cell, or can be part of a higher organized unit, for example, a plant tissue, plant organ, or plant. Thus, a plant cell can be a protoplast, a gamete producing cell, or a cell or collection of cells that can regenerate into a whole plant. A plant part includes plant tissue or any other groups of plant cells that is organized into a structural or functional unit.

As used herein, the term "progeny" refers to any plant resulting from a vegetative or sexual reproduction from one or more parent plants or descendants thereof. For instance, a progeny plant may be obtained by cloning or selfing of a parent plant or by crossing two parent plants and include selfings as well as the F1 or F2 or still further generations. An F1 is a first-generation progeny produced from parents at least one of which is used for the first time as donor of a trait, while offspring of second generation (F2) or subsequent generations (F3, F4, etc.) are specimens produced from selfings of F1's F2's etc. An F1 may thus be (and usually is) a hybrid resulting from a cross between two true breeding parents (true-breeding is homozygous for a trait), while an F2 may be (and usually is) a progeny resulting from self-pollination of said F1 hybrids.

A "single locus converted" or "single gene converted" plant refers to plants which are developed by a plant breeding technique called backcrossing or via genetic engineering wherein essentially all of the morphological and physiological characteristics of a variety are recovered in addition to the desired trait or characteristics conferred by the single locus transferred into the variety via the backcrossing technique or via genetic engineering. A single locus may comprise one gene, or in the case of transgenic plants, one or more transgenes integrated into the host genome at a single site (locus).

A "transgene" refers to a nucleic acid of interest that can be introduced into the genome of a plant by genetic engineering techniques (e.g., transformation).

*Triticale* Variety APT1415420

APT1415420 is a winter-type, awnless, short, hexaploidy *Triticale*. APT1415420 is a short *Triticale* ranging in plant height from 91-122 cm depending upon the environment. It is a winter-planted *Triticale* and late in maturity. APT1415420 is awnless. At maturity it has white glumes and amber seed. APT1415420 is derived from a cross made in 2005. Early generation selections were made using a modified bulk breeding method for such traits as height, maturity, disease tolerance, straw strength, and awnlessness. APT1415420 was tested in multiple locations including Texas, Montana, New York, Washington, Ohio, Pennsylvania, and Idaho from 2019-2021 and seed purification began in 2018.

The variety has shown uniformity and stability, as described in the following variety description information. The variety can have some taller, awnless variants at a frequency of less than 1.0% in subsequent generations. The following is a botanical description of the new variety of *Triticale* based on observations of various specimens grown in Texas, Montana, New York, Washington, Ohio, Pennsylvania, and Idaho.

TABLE 1

| Variety Description Information | |
| --- | --- |
| Growth Habit | |
| Spring/intermediate/winter | Winter |
| Juvenile plant growth | Semi-Prostrate |
| Photoperiod | Insensitive |

9

TABLE 1-continued

| Variety Description Information | |
|---|---|
| Use | Dual grain, feed and forage |
| Ploidy | Hexaploid, 42 2n chromosome number |
| Maturity | Late; 6 days later than '641512175' |
| Height | Short, average 103 cm; average 21 cm shorter than '841446398' |
| Plant color at boot stage | Blue-Green |
| Stem | |
| Anthocyanin | Absent |
| Neck hairiness | Slight |
| Shape of neck | Wavy |
| Leaves | |
| Flag leaf | Twisted |
| Waxy bloom on leaf at boot | Present |
| Leaf carriage | Upright |
| Auricle color | Colorless or White |
| Head | |
| Density | Dense |
| Shape | Fusiform |
| Awnedness | Awnless |
| Glumes at maturity | |
| Pubescence | Slightly Pubescent |
| Color | White |
| Length | Mid-long |
| Width | Narrow |
| Shoulder | Wanting |
| Beak | Acuminate |
| Coleoptile color | White |
| Seed | |
| Shape | Elliptical |
| Smoothness | Slightly wrinkled |
| Brush area | Mid-Size |
| Brush length | Mid-Long |
| Color | Amber |

Based on overall morphology, APT1415420 is most comparable to variety '841446398'. APT1415420 most clearly differs from '841446398' in maturity and plant height, as shown below in Table 2.

TABLE 2

| Trait | APT1415420 | '841446398' |
|---|---|---|
| Maturity (Julian Days) | 110 +/− 1 day | 108 +/− 1 day |
| Height (Average) | 103 cm | 124 cm |

The plant of *Triticale* variety APT1415420 and any part thereof can be useful in a wide variety of applications including, but not limited to, use for grazing, silage, feed, cover crops, straw, and even human consumption purposes including flours, brans, doughs, cereals, pastas, and the like. Additionally, production of *Triticale* provides environmental benefits such as erosion and weed control and improved nutrient cycling through crop rotation. *Triticale* has high nitrogen-acquisition capabilities, making it an ideal crop to grow in the off-season after other crops have left too much nitrogen in the soil.

A method of producing *Triticale* variety APT1415420 for use as a commodity plant product may comprise harvesting the commodity plant product from the plant. After harvesting, the commodity plant product may undergo further processing and/or packaging as appropriate for the intended use. *Triticale* variety APT1415420 may also be planted for the purposes of livestock grazing or for use as a cover crop in the off-season to control erosion and improve the soil nutrient profile.

The following describes breeding methods that may be used with cultivar APT1415420 in the development of further *Triticale* plants. One such embodiment is a method for developing an APT1415420 progeny *Triticale* plant in a *Triticale* plant breeding program comprising: obtaining the *Triticale* plant, or a part thereof, of cultivar APT1415420 utilizing said plant or plant part as a source of breeding material and selecting an APT1415420 progeny plant with molecular markers in common with APT1415420 and/or with morphological and/or physiological characteristics selected from those described above. As used herein, the term "plant" includes plant cells, plant protoplasts, plant cells of tissue culture from which *Triticale* plants can be regenerated, plant calli, plant clumps, and plant cells that are intact in plants or parts of plants, such as pollen, flowers, embryos, ovules, seeds, leaves, stems, roots, anthers and the like. Thus, another aspect of this invention is to provide for cells which upon growth and differentiation produce a cultivar having essentially all of the physiological and morphological characteristics of APT1415420.

This invention is also directed to methods for producing a *Triticale* plant by crossing a first parent *Triticale* plant with a second parent *Triticale* plant, wherein the first or second *Triticale* plant is the *Triticale* plant from the cultivar APT1415420. Further, the first or second parent may be a common wheat cultivar. Therefore, any methods using the cultivar APT1415420 are part of this invention: pedigree breeding, backcrosses, hybrid breeding, mutation breeding, recurrent selection, and crosses to populations. Any plants produced using APT1415420 as a parent are within the scope of this invention, including those developed from varieties derived from *Triticale* cultivar APT1415420. Advantageously, the *Triticale* cultivar could be used in crosses with other, different, *Triticale* plants to produce first generation ($F_1$) *Triticale* hybrid seeds and plants with superior characteristics. The cultivar of the invention can also be used for transformation where exogenous genes are introduced and expressed by the cultivar of the invention. Genetic variants created either through traditional breeding methods using cultivar APT1415420 or through transformation of APT1415420 by any of a number of protocols known to those of skill in the art are intended to be within the scope of this invention.

In conjunction with these steps, techniques such as RFLP-enhanced selection, genetic marker enhanced selection (for example SSR markers) and the making of double haploids may be utilized.

Another method involves producing a population of cultivar APT1415420 progeny *Triticale* plants, comprising crossing cultivar APT1415420 with another *Triticale* plant, thereby producing a population of *Triticale* plants, which, on average, derive 50% of their alleles from cultivar APT1415420. A plant of this population may be selected and repeatedly selfed or sibbed with a *Triticale* cultivar resulting from these successive filial generations. One embodiment of this invention is the *Triticale* cultivar produced by this method and that has obtained at least 50% of its alleles from cultivar APT1415420.

One of ordinary skill in the art of plant breeding would know how to evaluate the traits of two plant varieties to determine if there is no significant difference between the two traits expressed by those varieties. For example, see Fehr and Walt, Principles of Cultivar Development, p 261-286 (1987). Thus the invention includes *Triticale* cultivar APT1415420 progeny *Triticale* plants comprising a combination of at least two APT1415420 traits selected from the group consisting of those listed here so that said progeny

*Triticale* plant is not significantly different for said traits than *Triticale* cultivar APT1415420 as determined at the 5% significance level when grown in the same environment. Using techniques described herein, molecular markers may be used to identify said progeny plant as a APT1415420 progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of cultivar APT1415420 may also be characterized through their filial relationship with *Triticale* cultivar APT1415420, as for example, being within a certain number of breeding crosses of *Triticale* cultivar APT1415420. A breeding cross is a cross made to introduce new genetics into the progeny, and is distinguished from a cross, such as a self or a sib cross, made to select among existing genetic alleles. The lower the number of breeding crosses in the pedigree, the closer the relationship between *Triticale* cultivar APT1415420 and its progeny. For example, progeny produced by the methods described herein may be within 1, 2, 3, 4 or 5 breeding crosses of *Triticale* cultivar APT1415420.

The present compositions and methods contemplate a *Triticale* plant regenerated from a tissue culture of a cultivar (e.g., APT1415420) or hybrid plant of the present invention. As is well known in the art, tissue culture of *Triticale* can be used for the in vitro regeneration of a *Triticale* plant. Tissue culture of various tissues of plants and regeneration of plants therefrom is well known and widely published. For example, reference may be had to Komatsuda, T. et al., Crop Sci. 31:333-337 (1991); Stephens, P. A., et al., Theor. Appl. Genet 82:633-635 (1991); Komatsuda, T. et al., Plant Cell, Tissue and Organ Culture, 28:103-113 (1992); Dhir, S. et al. Plant Cell Reports 11:285-289 (1992); Pandey, P. et al., Japan J. Breed. 42:1-5 (1992); and Shetty, K., et al., Plant Science 81:245-251 (1992); as well as U.S. Pat. No. 5,024, 944 issued Jun. 18, 1991 to Collins et al., and U.S. Pat. No. 5,008,200 issued Apr. 16, 1991 to Ranch et al. Thus, another aspect of this invention is to provide cells which upon growth and differentiation produce *Triticale* plants having the physiological and morphological characteristics of *Triticale* cultivar APT1415420.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, ovules, pericarp, flowers, florets, heads, spikes, seeds, leaves, stems, roots, root tips, anthers, awns, stems, and the like. Means for preparing and maintaining plant tissue culture are well known in the art. By way of example, a tissue culture comprising organs has been used to produce regenerated plants. U.S. Pat. Nos. 5,959, 185, 5,973,234 and 5,977,445, describe certain techniques.

Methods of vegetatively (i.e. asexually) propagating a plant of *Triticale* variety APT1415420 or hybrid plant of the present invention are also provided. The methods may comprise collecting tissue capable of being propagated from a plant of *Triticale* variety APT1415420, cultivating the tissue to obtain proliferated shoots, and rooting the proliferated shoots to obtain rooted plantlets. Optionally the methods may further comprise growing plants from the rooted plantlets. Plantlets and plants produced by these methods, are encompassed by the disclosure.

Further Embodiments and Methods

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". many methods for producing transgenic plants have been developed, and the present invention, in particular embodiments, also relates to transformed versions of the claimed cultivar.

When referring to a transgene is meant to include a heterologous nucleic acid molecule which may be a heterologous polynucleotide or a heterologous nucleic acid or an exogenous DNA and includes a polynucleotide, nucleic acid or DNA segment that originates from a source foreign to the particular host cell, or, if from the same source, is modified from its original form in composition and/or genomic locus by human intervention. When referring to a gene or transgene that may be introduced into the plant is intended to include portions of the gene, and it may not include the entire gene, and may not include the native promoter or other components. By way of example without limitation, it can include sequences that are duplicates of those already in the plant cell, may be a modified version of the sequence, or its expression or function modified. A heterologous gene in a host cell includes a gene that is endogenous to the particular host cell, but has been modified or introduced into the plant. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides. As noted, a heterologous nucleic acid molecule may be introduced into the plant by any convenient methods. In one embodiment the heterologous nucleic acid molecule may be a transgene that is introduced by transformation.

The term introduced in the context of inserting a nucleic acid or polypeptide into a cell, includes transfection or transformation or transduction and includes reference to the incorporation of a nucleic acid into a cell where the nucleic acid may be incorporated into the genome of the cell (e.g., chromosome, plasmid, plastid or mitochondrial DNA), converted into an autonomous replicon, or transiently expressed (e.g., transfected mRNA). When referring to introduction of a nucleic acid sequence into a plant is meant to include transformation into the cell, as well as crossing a plant having the sequence with another plant, so that the second plant contains the heterologous sequence or transgene, as in conventional plant breeding techniques. Such breeding techniques are well known to one skilled in the art and examples are discussed herein. For a discussion of plant breeding techniques, see Poehlman (1995) *Breeding Field Crops*. AVI Publication Co., Westport Conn, 4th Edit.

Backcrossing methods may be used to introduce a gene into the plants. This technique has been used for decades to introduce traits into a plant. An example of a description of this and other plant breeding methodologies that are well known can be found in references such as Poehlman, supra, and *Plant Breeding Methodology*, edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent. Examples of such techniques and variations are set forth in further detail herein.

Various genetic elements can be introduced into the plant genome using transformation. These elements include, but are not limited to genes, coding sequences, inducible, constitutive, and tissue-specific promoters, enhancing sequences, and signal and targeting sequences.

In some embodiments, the invention comprises a APT1415420 plant that has been developed using both genetic engineering and traditional breeding techniques. For example, a genetic trait that may have been engineered into the genome of a particular *Triticale* plant may then be moved into the genome of a APT1415420 plant using traditional breeding techniques that are well known in the plant breeding arts. Likewise, a genetic trait that has been engineered into the genome of a APT1415420 plant may then be moved into the genome of another cultivar using traditional breeding techniques that are well known in the plant breeding arts. A backcrossing approach is commonly used to move a transgene or transgenes from a transformed *Triticale* cultivar into an already developed *Triticale* cultivar, and the resulting backcross conversion plant would then comprise the transgene(s).

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed *Triticale* plants, using transformation methods as described below to incorporate transgenes into the genetic material of the *Triticale* plant(s).

Expression Vectors for *Triticale* Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII), which, when under the control of plant regulatory signals confers resistance to kanamycin. Fraley et al., Proc. Natl. Acad. Sci. U.S.A., 80:4803 (1983). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford et al., Plant Physiol. 86:1216 (1988), Jones et al., Mol. Gen. Genet, 210:86 (1987), Svab et al., Plant Mol. Biol. 14:197 (1990) Hille et al., Plant Mol. Biol. 7:171 (1986). Other selectable marker genes confer resistance to herbicides such as glyphosate, glufosinate or bromoxynil. Comai et al., Nature 317:741-744 (1985), Gordon-Kamm et al., Plant Cell 2:603-618 (1990) and Stalker et al., Science 242:419-423 (1988).

Other selectable marker genes for plant transformation that are not of bacterial origin include, for example, mouse dihydrofolate reductase, plant 5-enolpyruvyl-shikimate-3-phosphate synthase and plant acetolactate synthase. Eichholtz et al., Somatic Cell Mol. Genet. 13:67 (1987), Shah et al., Science 233:478 (1986), Charest et al., Plant Cell Rep. 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include. beta.-glucuronidase (GUS), .beta.-galactosidase, luciferase and chloramphenicol acetyltransferase. Jefferson, R. A., Plant Mol. Biol. Rep. 5:387 (1987), Teeri et al., EMBO J. 8:343 (1989), Koncz et al., Proc. Natl. Acad. Sci U.S.A. 84:131 (1987), DeBlock et al., EMBO J. 3:1681 (1984).

In vivo methods for visualizing GUS activity that do not require destruction of plant tissue are available. Molecular Probes publication 2908, Imagene Green, p. 1-4 (1993) and Naleway et al., J. Cell Biol. 115:151a (1991). However, these in vivo methods for visualizing GUS activity have not proven useful for recovery of transformed cells because of low sensitivity, high fluorescent backgrounds and limitations associated with the use of luciferase genes as selectable markers.

The gene encoding Green Fluorescent Protein (GFP) has been utilized as a marker for gene expression in prokaryotic and eukaryotic cells. Chalfie et al., Science 263:802 (1994). GFP and mutants of GFP may be used as screenable markers.

Expression Vectors for *Triticale* Transformation: Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters.

A "constitutive" promoter is a promoter which is active under most environmental conditions. A constitutive promoter is operably linked to a gene for expression in wheat, or is operably linked to a nucleotide sequence encoding a signal sequence that is operably linked to a gene for expression in *Triticale*. Many different constitutive promoters are available. Exemplary constitutive promoters include, but are not limited to, the promoters from plant viruses, such as the 35S promoter from CaMV and the promoters from such genes as rice actin; ubiquitin; pEMU; MAS, and maize H3 histone. The ALS promoter, Xbal/Ncol fragment 5' to the *Brassica napus* ALS3 structural gene (or a nucleotide sequence similarity to said Xbal/Ncol fragment), represents a particularly useful constitutive promoter.

A tissue-specific promoter or tissue-preferred promoter may be operably linked to a gene for expression in *Triticale*. Plants transformed with a gene of interest operably linked to a tissue-specific promoter may produce the protein product of the transgene exclusively, or preferentially, in a specific tissue. Any tissue-specific or tissue-preferred promoter can be utilized in the present invention. Exemplary tissue-specific or tissue-preferred promoters include, but are not limited to, a root-preferred promoter, such as that from the phaseolin gene; a leaf-specific and light-induced promoter, such as that from cab or rubisco; an anther-specific promoter, such as that from LAT52; a pollen-specific promoter, such as that from Zml 3; or a microspore-preferred promoter, such as that from apg.

An inducible regulatory element is one that is capable of directly or indirectly activating transcription of one or more DNA sequences or genes in response to an inducer. In the absence of an inducer the DNA sequences or genes will not be transcribed. Any inducible promoter may be used in the present invention. Exemplary inducible promoters include, but are not limited to, those from the ACEI system, which respond to copper, and the In2 gene from maize, which responds to benzene-sulfonamide herbicide safeners. In an embodiment, the inducible promoter may be a promoter that responds to an inducing agent to which plants do not normally respond. An exemplary inducible promoter may be an inducible promoter from a steroid hormone gene, the transcriptional activity of which is induced by a glucocorticosteroid hormone.

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., Plant Mol. Biol. 20:49 (1992); Close, P. S., Master's Thesis, Iowa State University (1993); Knox, C., et al., Plant Mol. Biol. 9:3-17 (1987); Lerner et al., Plant Physiol. 91:124-129 (1989); Fontes et al., Plant Cell 3:483-496 (1991); Matsuoka et al., Proc. Natl. Acad. Sci. 88:834 (1991); Gould et al., J. Cell. Biol. 108:1657 (1989); Creissen et al., Plant J. 2:129 (1991); Kalderon, et al., Cell 39:499-509 (1984); Steifel, et al., Plant Cell 2:785-793 (1990).

Heterologous Protein Genes and Agronomic Genes

With transgenic plants, a heterologous protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981). According to an embodiment, the transgenic plant provided for commercial production of foreign protein is a *Triticale* plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269: 284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266:789 (1994) (cloning of the *tomato* Cf-9 gene for resistance to *Cladosporium fulvum*); Martin et al., Science 262:1432 (1993) (*tomato* Pto gene for resistance to *Pseudomonas syringae* pv. *tomato* encodes a protein kinase); Mindrinos et al., Cell 78:1089 (1994) (*Arabidopsis* RSP2 gene for resistance to *Pseudomonas syringae*).

B. A gene conferring resistance to a pest, such as nematodes. See e.g., PCT Application WO 96/30517; PCT Application WO 93/19181.

B. A *Bacillus thuringiensis* protein, a derivative thereof or a synthetic polypeptide modelled thereon. See, for example, Geiser et al., Gene, 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

C. A lectin. See, for example, Van Damme et al., Plant Molec. Biol., 24:25 (1994), who disclose the nucleotide sequences of several *Clivia miniata* mannose-binding lectin genes.

D. A vitamin-binding protein such as avidin. See, PCT Application US 93/06487, which teaches the use of avidin and avidin homologues as larvicides against insect pests.

E. An enzyme inhibitor, for example, a protease or proteinase inhibitor or an amylase inhibitor. See, for example, Abe et al., J. Biol. Chem., 262:16793 (1987) (nucleotide sequence of rice cysteine proteinase inhibitor); Huub et al., Plant Molec. Biol., 21:985 (1993) (nucleotide sequence of cDNA encoding tobacco proteinase inhibitor I); Sumitani et al., Biosci. Biotech. Biochem., 57:1243 (1993) (nucleotide sequence of *Streptomyces nitrosporeus* α-amylase inhibitor); and U.S. Pat. No. 5,494,813 (Hepher and Atkinson, issued Feb. 27, 1996).

E. An insect-specific hormone or pheromone, such as an ecdysteroid or juvenile hormone, a variant thereof, a mimetic based thereon, or an antagonist or agonist thereof. See, for example, the disclosure by Hammock et al., Nature, 344:458 (1990), of baculovirus expression of cloned juvenile hormone esterase, an inactivator of juvenile hormone.

F. An insect-specific peptide or neuropeptide which, upon expression, disrupts the physiology of the affected pest. For example, see the disclosures of Regan, J. Biol. Chem., 269:9 (1994) (expression cloning yields DNA coding for insect diuretic hormone receptor); Pratt et al., Biochem. Biophys. Res. Comm., 163:1243 (1989) (an allostatin is identified in *Diploptera puntata*); Chattopadhyay et al., Critical Reviews in Microbiology, 30(1):33-54 (2004); Zjawiony, J Nat Prod, 67(2):300-310 (2004); Carlini & Grossi-de-Sa, Toxicon, 40(11):1515-1539 (2002); Ussuf et al., Curr Sci., 80(7):847-853 (2001); Vasconcelos & Oliveira, Toxicon, 44(4):385-403 (2004). See also, U.S. Pat. No. 5,266,317 to Tomalski et al., which discloses genes encoding insect-specific, paralytic neurotoxins.

G. An insect-specific venom produced in nature by a snake, a wasp, etc. For example, see, Pang et al., Gene, 116:165 (1992), for disclosure of heterologous expression in plants of a gene coding for a scorpion insectotoxic peptide.

H. An enzyme responsible for a hyperaccumulation of a monoterpene, a sesquiterpene, a steroid, hydroxamic acid, a phenylpropanoid derivative, or another non-protein molecule with insecticidal activity.

I. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See, PCT Application WO 93/02197 (Scott et al.), which discloses the nucleotide sequence of a callase gene. DNA molecules which contain chitinase-encoding sequences can be obtained, for example, from the ATCC under Accession Nos. 39637 and 67152. See also, Kramer et al., Insect Biochem. Molec. Biol., 23:691 (1993), who teach the nucleotide sequence of a cDNA encoding tobacco hornworm chitinase, and Kawalleck et al., Plant Molec. Biol., 21:673 (1993), who provide the nucleotide sequence of the parsley ubi4-2 polyubiquitin gene, U.S. Pat. Nos. 7,145,060, 7,087, 810, and 6,563,020.

J. A molecule that stimulates signal transduction. For example, see the disclosure by Botella et al., Plant Molec. Biol., 24:757 (1994), of nucleotide sequences for mung bean calmodulin cDNA clones, and Griess et al., Plant Physiol., 104:1467 (1994), who provide the nucleotide sequence of a maize calmodulin cDNA clone.

K. A hydrophobic moment peptide. See, PCT Application WO 95/16776 and U.S. Pat. No. 5,580,852, which disclose peptide derivatives of tachyplesin which inhibit fungal plant pathogens, and PCT Application WO 95/18855 and U.S. Pat. No. 5,607,914 which teaches synthetic antimicrobial peptides that confer disease resistance.

L. A membrane permease, a channel former or a channel blocker. For example, see the disclosure of Jaynes et al., Plant Sci, 89:43 (1993), of heterologous expression of a cecropin-β lytic peptide analog to render transgenic tobacco plants resistant to *Pseudomonas solanacearum*.

M. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy et al., Ann. Rev. Phytopathol., 28:451 (1990). Coat protein-mediated resistance has been conferred upon transformed plants against alfalfa mosaic virus, cucumber mosaic virus, and tobacco mosaic virus.

N. An insect-specific antibody or an immunotoxin derived therefrom. Thus, an antibody targeted to a critical metabolic function in the insect gut would inactivate an affected enzyme, killing the insect. See, Taylor et al., Abstract #497, Seventh Int'l Symposium on Molecular Plant-Microbe Interactions (Edinburgh, Scotland 1994) (enzymatic inactivation in transgenic tobacco via production of single-chain antibody fragments).

O. A virus-specific antibody. See, for example, Tavladoraki et al., Nature, 366:469 (1993), who show that transgenic plants expressing recombinant antibody genes are protected from virus attack.

P. A developmental-arrestive protein produced in nature by a pathogen or a parasite. Thus, fungal endo-α-1, 4-D-polygalacturonases facilitate fungal colonization and plant nutrient release by solubilizing plant cell wall homo-α-1,4-D-galacturonase. See, Lamb et al., Bio/Technology, 10:1436 (1992). The cloning and characterization of a gene which encodes a bean endopolygalacturonase-inhibiting protein is described by Toubart et al., Plant J., 2:367 (1992).

Q. A developmental-arrestive protein produced in nature by a plant. For example, Logemann et al., Bio/Technology, 10:305 (1992), have shown that transgenic plants expressing the barley ribosome-inactivating gene have an increased resistance to fungal disease.

R. Genes involved in the Systemic Acquired Resistance (SAR) Response and/or the pathogenesis-related genes. Briggs, S., Current Biology, 5(2) (1995); Pieterse & Van Loon, Curr. Opin. Plant Bio., 7(4):456-64 (2004); and Somssich, Cell, 113(7):815-6 (2003).

S. Antifungal genes. See, Cornelissen and Melchers, Plant Physiol., 101:709-712 (1993); Parijs et al., Planta, 183:258-264 (1991); and Bushnell et al., Can. J. of Plant Path., 20(2):137-149 (1998). See also, U.S. Pat. No. 6,875,907.

T. Cystatin and cysteine proteinase inhibitors. See, U.S. Pat. No. 7,205,453.

U. Defensin genes. See, WO 03/000863 and U.S. Pat. No. 6,911,577.

Any of the above-listed disease or pest resistance genes can be introduced into the claimed *Triticale* variety through a variety of means including, but not limited to, transformation and crossing.

2. Genes that Confer Resistance to an Herbicide:

A. An herbicide that inhibits the growing point or meristem, such as an imidazolinone or a sulfonylurea. Exemplary genes in this category code for mutant ALS and AHAS enzyme as described, for example, by Lee et al., EMBO J., 7:1241 (1988) and Miki et al., Theor. Appl. Genet., 80:449 (1990), respectively.

B. Glyphosate (resistance conferred by mutant 5-enolpyruvlshikimate-3-phosphate synthase (EPSP) and aroA genes, respectively) and other phosphono compounds such as glufosinate (phosphinothricin acetyl transferase (PAT) and *Streptomyces hygroscopicus* PAT, bar, genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., Bio/Technology 7:61 (1989), describe the production of transgenic plants that express chimeric bar genes coding for PAT activity. Exemplary of genes conferring resistance to phenoxy proprionic acids and cyclohexones, such as sethoxydim and haloxyfop are the Accl-S1, Accl-S2 and Accl-S3 genes described by Marshall et al., Theor. Appl. Genet. 83:435 (1992).

C. An herbicide that inhibits photosynthesis, such as a triazine (psbA and gs+ genes) and a benzonitrile (nitrilase gene). Przibila et al., *Plant Cell,* 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441, and 67442. Cloning and expression of DNA coding for a glutathione S-transferase is described by Hayes et al., *Biochem. J.,* 285:173 (1992).

D. Acetohydroxy acid synthase, which has been found to make plants that express this enzyme resistant to multiple types of herbicides, has been introduced into a variety of plants. See, Hattori et al., *Mol. Gen. Genet.,* 246:419 (1995). Other genes that confer tolerance to herbicides include a gene encoding a chimeric protein of rat cytochrome P4507A1 and yeast NADPH-cytochrome P450 oxidoreductase (Shiota et al., *Plant Physiol.,* 106:17 (1994)); genes for glutathione reductase and superoxide dismutase (Aono et al., *Plant Cell Physiol.,* 36:1687 (1995)); and genes for various phosphotransferases (Datta et al., *Plant Mol. Biol.,* 20:619 (1992)).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282, 837, 5,767,373, and International Publication WO 01/12825.

Any of the above listed herbicide genes can be introduced into the claimed *Triticale* variety through a variety of means including but not limited to transformation and crossing.

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., Proc. Nat. Acad. Sci. U.S.A. 89:2624 (1992).

B. Decreased phytate content—1) Introduction of a phytase-encoding gene would enhance breakdown of phytate, adding more free phosphate to the transformed plant. For example, see Van Hartingsveldt et al., Gene 127:87 (1993), for a disclosure of the nucleotide sequence of an *Aspergillus niger* phytase gene. 2) A gene could be introduced that reduced phytate content. In maize, this, for example, could be accomplished, by cloning and then reintroducing DNA associated with the single allele which is responsible for maize mutants characterized by low levels of phytic acid. See Raboy et al., Maydica 35:383 (1990).

C. Modified carbohydrate composition effected, for example, by transforming plants with a gene coding for an enzyme that alters the branching pattern of starch. See Shiroza et al., J. Bacteol. 170:810 (1988) (nucleotide sequence of *Streptococcus* mutants fructosyltransferase gene), Steinmetz et al., Mol. Gen. Genet. 20:220 (1985) (nucleotide sequence of *Bacillus subtilis* levansucrase gene), Pen et al., Bio/Technology 10:292 (1992) (production of transgenic plants that express *Bacillus lichenifonnis*. alpha.-amylase), Elliot et al., Plant Molec. Biol. 21:515 (1993) (nucleotide sequences of *tomato* invertase genes), SOgaard et al., J. Biol. Chem. 268:22480 (1993) (site-directed mutagenesis of barley .alpha.-amylase gene), and Fisher et al., Plant Physiol. 102:1045 (1993) (maize endosperm starch branching enzyme II).

D. Elevated oleic acid via FAD-2 gene modification and/or decreased linolenic acid via FAD-3 gene modification. See U.S. Pat. Nos. 6,063,947; 6,323,392; and international publication WO 93/11245.

E. The content of high-molecular weight gluten subunits (HMS-GS). Genomic clones have been isolated for different subunits (Anderson et al., In Proceedings of the 7.sup.th International Wheat Genetics Symposium, IPR, pp. 699-704, 1988; Shewry et al. In Oxford Surveys of Plant Molecular and Cell Biology, pp. 163-219, 1989; Shewry et al. Journal of Cereal Sci. 15:105-120, 1992). Blechl et al. (Journal of Plant Phys. 152 (6): 703-707, 1998) have transformed wheat with genes that encode a modified HMW-GS. See also U.S. Pat. Nos. 5,650,558; 5,914,450; 5,985,352; 6,174,725; and 6,252,134, which are incorporated herein by reference for this purpose.

4. Genes that Control Male Sterility

A. Introduction of a deacetylase gene under the control of a tapetum-specific promoter and with the application of the chemical N—Ac—PPT. See international publication WO 01/29237.

B. Introduction of various stamen-specific promoters. See international publications WO 92/13956 and WO 92/13957.

C. Introduction of the barnase and the barstar genes. See Paul et al., Plant Mol. Biol. 19:611-622, 1992).

D. Introduction of mitochondrial genes that are associated with the male sterile phenotype. Such genes may include mitochondrial Atp synthase 8-1 gene (Atp8-1), NAD9

NAD7 mitochondrial nicotinamide adenine dinucleotide dehydrogenase (NAD9), and NADH dehydrogenase subunit 4L (NAD4L), or functional fragments thereof, such as but not limited to, the male sterility associated mitochondrial genes listed in SEQ ID NOs: 32, 48, 64, 66, and 68 of U.S. Ser. No. 16/949,918 published May 27, 2021, which is incorporated herein by reference for this purpose.

Methods for *Triticale* Transformation

The methods disclosed herein comprise introducing a polypeptide or polynucleotide into a plant cell. "Introducing" is intended to mean presenting to the plant the polynucleotide or polypeptide in such a manner that the sequence gains access to the interior of a cell. The methods disclosed herein do not depend on a particular method for introducing a sequence into the host cell, only that the polynucleotide or polypeptides gains access to the interior of at least one cell of the host. Methods for introducing polynucleotide or polypeptides into host cells (i.e., plants) are known in the art and include, but are not limited to, stable transformation methods, transient transformation methods, and virus-mediated methods.

"Stable transformation" is intended to mean that the nucleotide construct introduced into a host (i.e., a plant) integrates into the genome of the plant and is capable of being inherited by the progeny thereof. "Transient transformation" is intended to mean that a polynucleotide or polypeptide is introduced into the host (i.e., a plant) and expressed temporally.

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., Science 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci. 10:1 (1991). Descriptions of *Agrobacterium* vector systems and methods for *Agrobacterium*-mediated gene transfer are provided by Gruber et al., supra, Miki et al., supra, and Moloney et al., Plant Cell Reports 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes. Sanford et al., Part. Sci. Technol. 5:27 (1987), Sanford, J. C., Trends Biotech. 6:299 (1988), Klein et al., Bio/Technology 6:559-563 (1988), Sanford, J. C., Physiol Plant 7:206 (1990), Klein et al., Biotechnology 10:268 (1992). See also U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang et al., Bio/Technology 9:996 (1991). Alternatively, liposome and spheroplast fusion have been used to introduce expression vectors into plants. Deshayes et al., EMBO J, 4:2731 (1985), Christou et al., Proc Natl. Acad. Sci. U.S.A. 84:3962 (1987). Direct uptake of DNA into protoplasts using $CaCl_2$ precipitation, polyvinyl alcohol or poly-L-omithine has also been reported. Hain et al., Mol. Gen. Genet. 199:161 (1985) and Draper et al., Plant Cell Physiol. 23:451 (1982). Electroporation of protoplasts and whole cells and tissues has also been described. Donn et al., In Abstracts of VIIth International Congress on Plant Cell and Tissue Culture IAPTC, A2-38, p 53 (1990); D'Halluin et al., Plant Cell 4:1495-1505 (1992) and Spencer et al., Plant Mol. Biol. 24:51-61 (1994).

Following transformation of *Triticale* target tissues, expression of the above-described selectable marker genes allows for preferential selection of transformed cells, tissues and/or plants, using regeneration and selection methods now well known in the art.

The foregoing methods for transformation would typically be used for producing a transgenic variety. The transgenic variety could then be crossed, with another (non-transformed or transformed) variety, in order to produce a new transgenic variety. Alternatively, a genetic trait which has been engineered into a particular *Triticale* cultivar using the foregoing transformation techniques could be moved into another cultivar using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Genetic Marker Profile Through SSR and First Generation Progeny

In addition to phenotypic observations, a plant can also be identified by its genotype. The genotype of a plant can be characterized through a genetic marker profile, which can identify plants of the same variety or a related variety or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as microsatellites, and Single Nucleotide Polymorphisms (SNPs).

Particular markers used for these purposes are not limited to any particular set of markers, but are envisioned to include any type of marker and marker profile that provides a means of distinguishing varieties. One method of comparison is to use only homozygous loci for APT1415420.

In addition to being used for identification of *Triticale* cultivar APT1415420 and plant parts and plant cells of cultivar APT1415420, the genetic profile may be used to identify a *Triticale* plant produced through the use of APT1415420 or to verify a pedigree for progeny plants produced through the use of APT1415420. The genetic marker profile can also be useful in breeding and developing backcross conversions.

Means of performing genetic marker profiles using SSR polymorphisms are known. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. PCR detection uses two oligonucleotide primers flanking the polymorphic segment of repetitive DNA. Repeated cycles of heat denaturation of the DNA, followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties, all SSR profiles may be performed in the same lab.

The SSR profile of *Triticale* plant APT1415420 can be used to identify plants comprising APT1415420 as a parent, since such plants will comprise the same homozygous alleles as APT1415420. Because the *Triticale* variety is essentially homozygous at all relevant loci, most loci should have only one type of allele present. In contrast, a genetic marker profile of an $F_1$ progeny should be the sum of those parents, e.g., if one parent was homozygous for allele x at a particular locus, and the other parent homozygous for allele y at that locus, then the $F_1$ progeny will be xy (heterozygous) at that locus. Subsequent generations of progeny produced by selection and breeding are expected to be of genotype x (homozygous), y (homozygous), or xy (heterozygous) for that locus position. When the $F_1$ plant is selfed or sibbed for successive filial generations, the locus should be either x or y for that position.

In addition, plants and plant parts substantially benefiting from the use of APT1415420 in their development, such as APT1415420 comprising a backcross conversion, transgene, or genetic sterility factor, may be identified by having a molecular marker profile with a high percent identity to APT1415420. In an embodiment, such a percent identity might be 95%, 96%, 97%, 98%, 99%, 99.5%, or 99.9% identical to APT1415420.

The SSR profile of APT1415420 also can be used to identify essentially derived varieties and other progeny varieties developed from the use of APT1415420, as well as cells and other plant parts thereof. Progeny plants and plant parts produced using APT1415420 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from APT1415420, as measured by either percent identity or percent similarity. Such progeny may be further characterized as being within a pedigree distance of APT1415420, such as within 1, 2, 3, 4, 5, or more cross pollinations to a

*Triticale* plant other than APT1415420 or a plant that has APT1415420 as a progenitor. Unique molecular profiles may be identified with other molecular tools such as SNPs and RFLPs.

While determining the SSR genetic marker profile of a plant as described above, several unique SSR profiles may also be identified that did not appear in either parent plant. Such unique SSR profiles may arise during the breeding process from recombination or mutation. A combination of several unique alleles provides a means of identifying a plant variety, an $F_1$ progeny produced from such variety, and further progeny produced from such variety.

Genome Editing

The terms "target site", "target sequence", "target DNA", "target locus", "genomic target site", "genomic target sequence", and "genomic target locus" are used interchangeably herein and refer to a polynucleotide sequence in the genome (including chloroplast and mitochondrial DNA) of a cell at which a double-strand break is induced in the cell genome. The target site can be an endogenous site in the genome of a cell or organism, or alternatively, the target site can be heterologous to the cell or organism and thereby not be naturally occurring in the genome, or the target site can be found in a heterologous genomic location compared to where it occurs in nature. As used herein, terms "endogenous target sequence" and "native target sequence" are used interchangeably herein to refer to a target sequence that is endogenous or native to the genome of a cell or organism and is at the endogenous or native position of that target sequence in the genome of a cell or organism. Cells include plant cells as well as plants and seeds produced by the methods described herein.

In one embodiments, the target site, in association with the particular gene editing system that is being used, can be similar to a DNA recognition site or target site that is specifically recognized and/or bound by a double-strand-break-inducing agent, such as but not limited to a Zinc Finger endonuclease, a meganuclease, a TALEN endonuclease, a CRISPR-Cas guideRNA or other polynucleotide guided double strand break reagent.

The terms "artificial target site" and "artificial target sequence" are used interchangeably herein and refer to a target sequence that has been introduced into the genome of a cell or organism. Such an artificial target sequence can be identical in sequence to an endogenous or native target sequence in the genome of a cell but be located in a different position (i.e., a non-endogenous or non-native position) in the genome of a cell or organism.

The terms "altered target site", "altered target sequence", "modified target site", and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Certain embodiments comprise polynucleotides disclosed herein which are modified using endonucleases. Endonucleases are enzymes that cleave the phosphodiester bond within a polynucleotide chain, and include restriction endonucleases that cleave DNA at specific sites without damaging the bases. Restriction endonucleases include Type I, Type II, Type III, and Type IV endonucleases, which further include subtypes. In the Type I and Type III systems, both the methylase and restriction activities are contained in a single complex.

Endonucleases also include meganucleases, also known as homing endonucleases (HEases). Like restriction endonucleases, HEases bind and cut at a specific recognition site. However, the recognition sites for meganucleases are typically longer, about 18 bp or more. (See patent publication WO2012/129373 filed on Mar. 22, 2012). Meganucleases have been classified into four families based on conserved sequence motifs (Belfort M, and Perlman P S J. Biol. Chem. 1995; 270:30237-30240). These motifs participate in the coordination of metal ions and hydrolysis of phosphodiester bonds. HEases are notable for their long recognition sites, and for tolerating some sequence polymorphisms in their DNA substrates.

The naming convention for meganucleases is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. This cleaving activity can be used to produce a double-strand break. For reviews of site-specific recombinases and their recognition sites, see, Sauer (1994) Curr. Op. Biotechnol. 5:521-7; and Sadowski (1993) FASEB 7:760-7. In some examples the recombinase is from the Integrase or Resolvase families.

TAL effector nucleases are a class of sequence-specific nucleases that can be used to make double-strand breaks at specific target sequences in the genome of a plant or other organism. (Miller et al. (2011) Nature Biotechnology 29:143-148). Zinc finger nucleases (ZFNs) are engineered double-strand-break-inducing agents comprised of a zinc finger DNA binding domain and a double-strand-break-inducing agent domain. Recognition site specificity is conferred by the zinc finger domain, which typically comprises two, three, or four zinc fingers, for example having a C2H2 structure; however other zinc finger structures are known and have been engineered. Zinc finger domains are amenable for designing polypeptides which specifically bind a selected polynucleotide recognition sequence. ZFNs include engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3-finger domain recognizes a sequence of 9 contiguous nucleotides; with a dimerization requirement of the nuclease, two sets of zinc finger triplets are used to bind an 18-nucleotide recognition sequence.

CRISPR loci (Clustered Regularly Interspaced Short Palindromic Repeats) (also known as SPIDRs—SPacer Interspersed Direct Repeats) constitute a family of recently described DNA loci. CRISPR loci consist of short and highly conserved DNA repeats (typically 24 to 40 bp, repeated from 1 to 140 times—also referred to as CRISPR-repeats) which are partially palindromic. The repeated sequences (usually specific to a species) are interspaced by variable sequences of constant length (typically 20 to 58 by depending on the CRISPR locus (WO2007/025097 published Mar. 1, 2007).

CRISPR loci were first recognized in *E. coli* (Ishino et al. (1987) J. Bacterial. 169:5429-5433; Nakata et al. (1989) J. Bacterial. 171:3553-3556). Similar interspersed short sequence repeats have been identified in *Haloferax medi-*

*terranei, Streptococcus pyogenes, Anabaena,* and *Mycobacterium tuberculosis* (Groenen et al. (1993) Mol. Microbiol. 10:1057-1065; Hoe et al. (1999) Emerg. Infect. Dis. 5:254-263; Masepohl et al. (1996) Biochim. Biophys. Acta 1307: 26-30; Mojica et al. (1995) Mol. Microbiol. 17:85-93). The CRISPR loci differ from other SSRs by the structure of the repeats, which have been termed short regularly spaced repeats (SRSRs) (Janssen et al. (2002) OMICS J. Integ. Biol. 6:23-33; Mojica et al. (2000) Mol. Microbiol. 36:244-246). The repeats are short elements that occur in clusters, that are always regularly spaced by variable sequences of constant length (Mojica et al. (2000) Mol. Microbiol. 36:244-246).

Cas gene relates to a gene that is generally coupled, associated or close to or in the vicinity of flanking CRISPR loci. The terms "Cas gene", "CRISPR-associated (Cas) gene" are used interchangeably herein. A comprehensive review of the Cas protein family is presented in Haft et al. (2005) Computational Biology, PLoS Comput Biol 1(6): e60. doi:10.1371/journal.pcbi.0010060. As described therein, 41 CRISPR-associated (Cas) gene families are described, in addition to the four previously known gene families. It shows that CRISPR systems belong to different classes, with different repeat patterns, sets of genes, and species ranges. The number of Cas genes at a given CRISPR locus can vary between species.

Cas endonuclease relates to a Cas protein encoded by a Cas gene, wherein said Cas protein is capable of introducing a double strand break into a DNA target sequence. The Cas endonuclease is guided by a guide polynucleotide to recognize and optionally introduce a double strand break at a specific target site into the genome of a cell (U.S. Provisional Application No. 62/023,239, filed Jul. 11, 2014). The guide polynucleotide/Cas endonuclease system includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA if a correct protospacer-adjacent motif (PAM) is approximately oriented at the 3' end of the target sequence.

The Cas endonuclease gene can be Cas9 endonuclease, or a functional fragment thereof, such as but not limited to, Cas9 genes listed in SEQ ID NOs: 462, 474, 489, 494, 499, 505, and 518 of WO2007/025097 published Mar. 1, 2007. The Cas endonuclease gene can be a plant, maize or soybean optimized Cas9 endonuclease, such as but not limited to a plant codon optimized *Streptococcus pyogenes* Cas9 gene that can recognize any genomic sequence of the form N(12-30)NGG. The Cas endonuclease can be introduced directly into a cell by any method known in the art, for example, but not limited to transient introduction methods, transfection and/or topical application.

As used herein, the term "guide RNA" relates to a synthetic fusion of two RNA molecules, a crRNA (CRISPR RNA) comprising a variable targeting domain, and a tracrRNA. In one embodiment, the guide RNA comprises a variable targeting domain of 12 to 30 nucleotide sequences and a RNA fragment that can interact with a Cas endonuclease.

As used herein, the term "guide polynucleotide", relates to a polynucleotide sequence that can form a complex with a Cas endonuclease and enables the Cas endonuclease to recognize and optionally cleave a DNA target site (U.S. Provisional Application No. 62/023,239, filed Jul. 11, 2014). The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotride that solely comprises ribonucleic acids is also referred to as a "guide RNA".

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA-combination sequences. In some embodiments, the first molecule of the duplex guide polynucleotide comprising a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the cRNA naturally occurring in Bacteria and Archaea. In one embodiment, the size of the fragment of the cRNA naturally occurring in Bacteria and Archaea that is present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides. In one embodiment, the RNA that guides the RNA/Cas9 endonuclease complex, is a duplexed RNA comprising a duplex crRNA-tracrRNA.

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In some embodiments the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). In one embodiment of the disclosure, the single guide RNA comprises a cRNA or cRNA fragment and a tracrRNA or tracrRNA fragment of the type II/Cas system that can form a complex with a type II Cas endonuclease, wherein said guide RNA/Cas endonuclease complex can direct the Cas endonuclease to a plant genomic target site, enabling the Cas endonuclease to introduce a double strand break into the genomic target site. One aspect of using a single guide polynucleotide versus a duplex guide polynucleotide is that only one expression cassette needs to be made to express the single guide polynucleotide.

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid
(LNA), a 5-methyl dC nucleotide, a 2,6-Diaminopurine
nucleotide, a 2'-Fluoro A nucleotide, a 2'-Fluoro U nucleo-
tide; a 2'-O-Methyl RNA nucleotide, a phosphorothioate
bond, linkage to a cholesterol molecule, linkage to a poly-
ethylene glycol molecule, linkage to a spacer 18 molecule,
a 5' to 3' covalent linkage, or any combination thereof. These
modifications can result in at least one additional beneficial
feature, wherein the additional beneficial feature is selected
from the group of a modified or regulated stability, a
subcellular targeting, tracking, a fluorescent label, a binding
site for a protein or protein complex, modified binding
affinity to complementary target sequence, modified resis-
tance to cellular degradation, and increased cellular perme-
ability.

In certain embodiments the nucleotide sequence to be
modified can be a regulatory sequence such as a promoter,
wherein the editing of the promoter comprises replacing the
promoter (also referred to as a "promoter swap" or "pro-
moter replacement") or promoter fragment with a different
promoter (also referred to as replacement promoter) or
promoter fragment (also referred to as replacement promoter
fragment), wherein the promoter replacement results in any
one of the following or any combination of the following: an
increased promoter activity, an increased promoter tissue
specificity, a decreased promoter activity, a decreased pro-
moter tissue specificity, a new promoter activity, an induc-
ible promoter activity, an extended window of gene expres-
sion, a modification of the timing or developmental progress
of gene expression in the same cell layer or other cell layer
(such as but not limiting to extending the timing of gene
expression in the tapetum of maize anthers; see e.g. U.S. Pat.
No. 5,837,850 issued Nov. 17, 1998), a mutation of DNA
binding elements and/or deletion or addition of DNA bind-
ing elements. The promoter (or promoter fragment) to be
modified can be a promoter (or promoter fragment) that is
endogenous, artificial, pre-existing, or transgenic to the cell
that is being edited. The replacement promoter (or replace-
ment promoter fragment) can be a promoter (or promoter
fragment) that is endogenous, artificial, pre-existing, or
transgenic to the cell that is being edited.

Promoter elements to be inserted can be, but are not
limited to, promoter core elements (such as, but not limited
to, a CAAT box, a CCAAT box, a Pribnow box, a and/or
TATA box, translational regulation sequences and/or a
repressor system for inducible expression (such as TET
operator repressor/operator/inducer elements, or Sulphony-
lUrea (Su) repressor/operator/inducer elements. The dehy-
dration-responsive element (DRE) was first identified as a
cis-acting promoter element in the promoter of the drought-
responsive gene rd29A, which contains a 9 bp conserved
core sequence, TACCGACAT (Yamaguchi-Shinozaki, K.,
and Shinozaki, K. (1994) Plant Cell 6, 251-264). Insertion of
DRE into an endogenous promoter may confer a drought
inducible expression of the downstream gene. Another
example is ABA-responsive elements (ABREs) which con-
tain a (C/T)ACGTGGC consensus sequence found to be
present in numerous ABA and/or stress-regulated genes
(Busk P. K., Pages M. (1998) Plant Mol. Biol. 37:425-435).
Insertion of 35S enhancer or MMV enhancer into an endog-
enous promoter region will increase gene expression (U.S.
Pat. No. 5,196,525). The promoter (or promoter element) to
be inserted can be a promoter (or promoter element) that is
endogenous, artificial, pre-existing, or transgenic to the cell
that is being edited.

Single-Locus Conversion

When the term "*Triticale* plant" is used in the context of
the present invention, this also includes any single locus
conversions of that variety. The term "single locus converted
plant" or "single gene converted plant" as used herein refers
to those *Triticale* plants which are developed by a plant
breeding technique called backcrossing or via genetic engi-
neering wherein essentially all of the desired morphological
and physiological characteristics of a variety are recovered
in addition to the single gene transferred into the variety via
the backcrossing technique or via genetic engineering.

Backcrossing methods can be used with the present
invention to improve or introduce a characteristic into the
variety. The term "backcrossing" as used herein refers to the
repeated crossing of a hybrid progeny back to the recurrent
parent, i.e., backcrossing 1, 2, 3, 4, 5, 6, 7, 8, 9 or more times
to the recurrent parent. The parental *Triticale* plant which
contributes the gene for the desired characteristic is termed
the "nonrecurrent" or "donor parent". This terminology
refers to the fact that the nonrecurrent parent is used one
time in the backcross protocol and therefore does not recur.
The parental *Triticale* plant to which the gene or genes from
the nonrecurrent parent are transferred is known as the
recurrent parent as it is used for several rounds in the
backcrossing protocol (Poehlman & Sleper, 1994; Fehr,
1987). In a typical backcross protocol, the original variety of
interest (recurrent parent) is crossed to a second variety
(nonrecurrent parent) that carries the single gene of interest
to be transferred. The resulting progeny from this cross are
then crossed again to the recurrent parent and the process is
repeated until a *Triticale* plant is obtained wherein essen-
tially all of the desired morphological and physiological
characteristics of the recurrent parent are recovered in the
converted plant, in addition to the single transferred gene
from the nonrecurrent parent, as determined at the 5%
significance level when grown in the same environmental
conditions.

The selection of a suitable recurrent parent is made for a
successful backcrossing procedure. The goal of a backcross
protocol is to alter or substitute a single trait or characteristic
in the original variety. To accomplish this, a single gene of
the recurrent variety is modified or substituted with the
desired gene from the nonrecurrent parent, while retaining
essentially all of the rest of the desired genetic, and therefore
the desired physiological and morphological, constitution of
the original variety. The choice of the particular nonrecur-
rent parent will depend on the purpose of the backcross. One
of the major purposes is to add some commercially desir-
able, agronomically important trait to the plant. The exact
backcrossing protocol will depend on the characteristic or
trait being altered to determine an appropriate testing pro-
tocol. Although backcrossing methods are simplified when
the characteristic being transferred is a dominant allele, a
recessive allele may also be transferred. In this instance it
may be necessary to introduce a test of the progeny to
determine if the desired characteristic has been successfully
transferred.

Many single gene traits have been identified that are not
regularly selected for in the development of a new variety
but that can be improved by backcrossing techniques. Single
gene traits may or may not be transgenic, examples of these
traits include but are not limited to, male sterility, waxy
starch, herbicide resistance, resistance for bacterial, fungal,
or viral disease, insect resistance, male fertility, enhanced
nutritional quality, industrial usage, yield stability and yield
enhancement. These genes are generally inherited through
the nucleus. Several of these single gene traits are described in U.S. Pat. Nos. 5,959,185, 5,973,234 and 5,977,445, the disclosures of which are specifically hereby incorporated by reference.

In particular embodiments of the invention, the single locus conversion may comprise a transgenic gene which has been introduced by genetic transformation into the *Triticale* cultivar APT1415420 or a progenitor thereof. In still other embodiments of the invention, the single locus conversion may comprise a dominant or recessive allele. The locus conversion may confer potentially any trait upon the single locus converted plant, including, but not limited to, herbicide resistance, insect resistance, resistance to bacterial, fungal, or viral disease, male fertility or sterility, and improved nutritional quality.

Deposit

A deposit of the seed of *Triticale* plant APT1415420 is and has been maintained by Northern Agri Brands, LLC, 205 9ᵗʰ Ave. S., Suite 205, Great Falls, Montana 59405, since prior to the filing date of this application. Access to this deposit will be available during the pendency of the application to the Commissioner of Patents and Trademarks and persons determined thereby to be entitled thereto upon request. Deposit will be made in a timely manner upon allowance of any claims in the application, whereby, the Applicant(s) will make available to the public, pursuant to 37 CFR 1.808(2), a deposit of at least 625 seeds of variety APT1415420 with the Provasoli-Guillard National Center for Marine Algae and Microbiota (NCMA), 60 Bigelow Drive, East Boothbay, ME 04544, USA, with NCMA Accession No. 202509138. The seeds deposited with the NCMA on Sep. 26, 2025 will be taken from the same deposit maintained at Northern Agri Brands, LLC and described above. Additionally, Applicant(s) will meet all the requirements of 37 C.F.R. § 1.801-1.809, including providing an indication of the viability of the sample when the deposit is made. These deposits will be maintained in the NCMA depository, which is a public depository, for a period of 30 years, or 5 years after the most recent request, or for the enforceable life of the patent, whichever is longer, and will be replaced if it ever becomes nonviable during that period. Applicant has no authority to waive any restrictions imposed by law on the transfer of biological material or its transportation in commerce. Applicant does not waive any infringement of its rights granted under this patent or under the Plant Variety Protection Act (7 USC 2321 et seq.).

What is claimed is:

1. A seed of *Triticale* cultivar APT1415420, wherein a representative sample of seed of said cultivar has been deposited under NCMA Accession No. 202509138.

2. A *Triticale* plant produced by growing the seed of claim 1.

3. A *Triticale* plant, or part thereof, having all the physiological and morphological characteristics of the *Triticale* plant of claim 2.

4. A part of the plant of claim 2, wherein said part comprises a head, awn, leaf, pollen, ovule, embryo, cotyledon, hypocotyl, meristematic cell, root, root tip, pistil, anther, floret, seed, pericarp, spike, stem, and/or callus.

5. A tissue culture of regenerable cells or protoplasts from the plant of claim 2.

6. The tissue culture of claim 5, wherein the cells of the tissue culture are produced from a plant part selected from the group of heads, awns, leaves, pollen, embryos, cotyledons, hypocotyls, meristematic cells, roots, root tips, pistils, anthers, flowers, stems, and calli.

7. A *Triticale* plant regenerated from the tissue culture of claim 5, wherein the plant has all the morphological and physiological characteristics of cultivar APT1415420, wherein a sample of seed of the cultivar was deposited under NCMA Accession No. 202509138.

8. A method of vegetatively propagating a plant of *Triticale* cultivar APT1415420, the method comprising:
a. collecting tissue capable of being propagated from a plant of *Triticale* cultivar APT1415420, wherein a sample of seed of the cultivar was deposited under NCMA Accession No. 202509138;
b. cultivating the tissue to obtain proliferated shoots to obtain rooted plantlets; and
c. optionally growing plants from the rooted plantlets.

9. A plant or rooted plantlet as produced by the method of claim 8.

10. A method of producing *Triticale* seed, wherein the method comprises crossing two *Triticale* plants and harvesting the resultant *Triticale* seed, wherein at least one *Triticale* plant is the *Triticale* plant of claim 2.

11. A *Triticale* seed produced by the method of claim 10.

12. A *Triticale* plant, or a part thereof, produced by growing the seed of claim 11, wherein said part comprises a head, awn, leaf, pollen, ovule, cotyledon, hypocotyl, meristematic cell, root, root tip, pistil, anther, floret, pericarp, spike, stem, and/or callus.

13. The method of claim 10, wherein the method further comprises crossing the plant of *Triticale* cultivar APT1415420 with a second, distinct *Triticale* plant to produce an $F_1$ hybrid *Triticale* seed.

14. The method of claim 13, further comprising:
a. crossing a plant grown from the $F_1$ hybrid *Triticale* seed with itself or a different *Triticale* plant to produce a seed of a first progeny plant of a second generation;
b. growing a plant from the seed of the first progeny plant of the second generation and crossing the first progeny plant of the second generation with itself or a second plant to produce a seed of a second progeny plant of a third generation; and
c. repeating steps (a) and (b) using the second progeny plant of the third generation from step (b) in place of the plant grown from the $F_1$ hybrid *Triticale* seed in step (a), wherein steps (a) and (b) are repeated with sufficient inbreeding to produce an inbred *Triticale* plant derived from the *Triticale* cultivar APT1415420.

15. A method of producing a *Triticale* plant derived from *Triticale* cultivar APT1415420, the method comprising:
a. crossing the plant of claim 2 with a second *Triticale* plant to produce a progeny plant;
b. crossing the progeny plant of step (a) with itself or the second *Triticale* plant in step (a) to produce a seed;
c. growing a progeny plant of a subsequent generation from the seed produced in step (b);
d. crossing the progeny plant of a subsequent generation of step (c) with itself or the second *Triticale* plant in step (a) to produce a *Triticale* plant derived from *Triticale* cultivar APT1415420.

16. A plant produced by introducing a single locus conversion into *Triticale* cultivar APT1415420, or a selfed progeny thereof comprising the single locus conversion, wherein the single locus conversion is introduced into the *Triticale* cultivar APT1415420 by backcrossing or genetic transformation and wherein a sample of seed of *Triticale* cultivar APT1415420 has been deposited under NCMA Accession No. 202509138.

17. The plant of claim 16, wherein the single locus conversion comprises a transgene.

18. A seed that produces the plant of claim 16.

19. The seed of claim 18, wherein the single locus confers a trait selected from the group consisting of male sterility, herbicide tolerance, insect resistance, pest resistance, disease resistance, modified fatty acid metabolism, abiotic stress resistance, altered seed amino acid composition, site-specific genetic recombination, and modified carbohydrate metabolism.

20. The seed of claim 19, wherein the single locus confers tolerance to an herbicide selected from the group consisting of glyphosate, sulfonylurea, imidazolinone, dicamba, glufosinate, phenoxy propionic acid, L-phosphinothricin, cyclohexanone, cyclohexanedione, triazine, and benzonitrile.

21. A method of producing a commodity plant product comprising collecting the commodity plant product from a plurality of plants of claim 2.

22. The method of claim 21, wherein the commodity plant product is grain, flour, bran, malt, hay, or silage.

23. A method of weed and erosion control comprising planting the *Triticale* plant of claim 2.

24. A method of introducing a desired trait into *Triticale* cultivar APT1415420 wherein the method comprises:

a. crossing a APT1415420 plant, wherein a representative sample of seed was deposited under NCMA Accession No. 202509138, with a plant of another *Triticale* cultivar that comprises a desired trait to produce an $F_1$ progeny plant;

b. selecting one or more $F_1$ progeny plants that have the desired trait to produce selected progeny plants;

c. crossing the selected progeny plants with the APT1415420 plants to produce backcross progeny plants;

d. selecting for backcross progeny plants that have the desired trait and otherwise all of the physiological and morphological characteristics of *Triticale* cultivar APT1415420 to produce selected backcross progeny plants; and e. repeating steps (c) and (d) three or more times in succession to produce selected fourth or higher backcross progeny plants that comprise the desired trait and otherwise all of the physiological and morphological characteristics of *Triticale* cultivar APT1415420.

25. The method of claim 24, wherein the desired trait is selected from the group consisting of male sterility, herbicide resistance, insect resistance, modified fatty acid metabolism, modified carbohydrate metabolism, modified phytic metabolism, modified waxy starch content, modified gluten content and resistance to bacterial disease, fungal disease or viral disease.

26. A *Triticale* plant or plant part produced by the method of claim 24, wherein the plant has the desired trait and otherwise all of the physiological and morphological characteristics of *Triticale* cultivar APT1415420.

27. The *Triticale* plant of claim 26, wherein the desired trait is male sterility and the trait is conferred by a cytoplasmic nucleic acid molecule that confers male sterility.

28. A method of producing a plant of *Triticale* cultivar APT1415420 comprising at least one new trait, the method comprising introducing a mutation or transgene conferring the at least one new trait into a plant of *Triticale* cultivar APT1415420, wherein a sample of seed of the cultivar has been deposited under NCMA Accession No. 202509138.

29. A method of introducing a mutagen into the genome of *Triticale* cultivar APT1415420, the method comprising applying a mutagen to the plant of claim 2, or a part thereof, wherein the mutagen is selected from ethyl methanesulfonate, gamma-rays, and sodium azide, and wherein the resulting plant comprises a genome mutation.

30. A method of producing a genetically modified *Triticale* plant, wherein the method comprises mutation, transformation, gene conversion, genome editing, RNA interference or gene silencing of the plant of claim 2.

31. A method for producing a male sterile *Triticale* plant, comprising transforming the *Triticale* plant of claim 2 with a nucleic acid molecule that confers male sterility.

32. A male sterile *Triticale* plant produced by the method of claim 31, wherein the plant is male sterile and otherwise has all the morphological and physiological characteristics of *Triticale* cultivar APT 1415420.

33. A method for developing a *Triticale* cultivar in a *Triticale* plant breeding program, comprising applying plant breeding techniques comprising recurrent selection, backcrossing, pedigree breeding, marker enhanced selection, mutation breeding, transformation, or genetic modification to the *Triticale* plant of claim 2, or its parts, wherein application of said techniques results in development of a *Triticale* cultivar.

34. An $F_1$ hybrid triticale seed produced by the method of claim 13.

* * * * *